United States Patent
Hosseinian et al.

(10) Patent No.: US 7,597,477 B1
(45) Date of Patent: Oct. 6, 2009

(54) HANDLEBARS FOR COMPUTERIZED TOMOGRAPHY SCANNER

(76) Inventors: Farahnaz B. Hosseinian, 18241 McCoy Ave., Saratoga, CA (US) 95070; Donya Hosseinian, 18241 McCoy Ave., Saratoga, CA (US) 95070; Marva Hosseinian, 18241 McCoy Ave., Saratoga, CA (US) 95070

(*) Notice: Subject to any disclaimer, the term of this patent is extended or adjusted under 35 U.S.C. 154(b) by 0 days.

(21) Appl. No.: 12/314,754

(22) Filed: Dec. 16, 2008

Related U.S. Application Data

(60) Provisional application No. 61/136,692, filed on Sep. 25, 2008.

(51) Int. Cl.
*H05G 1/00* (2006.01)

(52) U.S. Cl. .................... 378/208; 378/20

(58) Field of Classification Search ........... 378/4–20, 378/193–198, 204, 208, 209; 250/370.08, 250/370.09
See application file for complete search history.

(56) References Cited

U.S. PATENT DOCUMENTS

| | | | |
|---|---|---|---|
| 5,377,250 A | 12/1994 | Hu | 378/15 |
| 7,017,209 B1 | 3/2006 | De Jong et al. | 5/601 |
| 2008/0118132 A1 | 5/2008 | Ubelhart et al. | 382/131 |
| 2008/0192885 A1* | 8/2008 | Teofilovic et al. | 378/4 |

* cited by examiner

*Primary Examiner*—Courtney Thomas
(74) *Attorney, Agent, or Firm*—Richard C. Litman

(57) ABSTRACT

The handlebars for a computed tomography (CT) scanner are handlebars disposed on the face of the gantry of a CT scanner. The handlebars are to be utilized by patients who might have difficulty adjusting their arms to an optimum position for a CT scan. The handlebars are arranged in different patterns on the face of the gantry to accommodate patients of different arm lengths and/or various degrees of impairment.

14 Claims, 6 Drawing Sheets

HANDLEBARS FOR COMPUTERIZED TOMOGRAPHY SCANNER

CROSS-REFERENCE TO RELATED APPLICATION

This application claims the benefit of U.S. Provisional Patent Application Ser. No. 61/136,692, filed Sep. 25, 2008.

BACKGROUND OF THE INVENTION

1. Field of the Invention

The present invention generally relates to medical imaging devices, and more particularly to handlebars for a computed tomography scanner that provide patient support handlebars positioned on the face of a gantry of a computed tomography (CT) scanner.

2. Description of the Related Art

The advent of medical imaging machines has vastly improved the ability of medical personnel to diagnose and recommend precise treatment for a host of illnesses and injuries. In addition to CT, magnetic resonance imaging (MRI) and positron emission tomography (PET) have become invaluable diagnostic tools in the medical area. Unfortunately, many patients encounter problems when attempting to utilize a cross-sectional imaging device, such as a CT machine. Patients with a limited range of motion in their shoulders and/or arms, patients with arthritis, patients who have difficulty straightening their elbows over their heads, and patients who have problems holding their arms still and straight during the I.V. contrast injection phase of the procedure all experience various degrees of discomfort and difficulty. Such discomfort and difficulty can cause additional time and medical personnel involvement to obtain an ideal CT scan that, in turn, translate into reduced efficiency and increased cost. The medical arts would certainly welcome an adjunct that could be economically applied to existing and new CT scanners and that would enhance comfort for both normal and impaired patients, and which would also save time and reduce the risk of injection failure. Thus, handlebars for a computed topography scanner solving the aforementioned problems are desired.

SUMMARY OF THE INVENTION

The handlebars for a computed tomography scanner are handlebars positioned on the front face of the gantry of a CT scanner. The handlebars are to be utilized by patients who might have difficulty adjusting their arms to an optimum position for a CT scan. The handlebars may be arranged in different patterns on the face of the gantry to accommodate patients of different arm lengths and/or various degrees of impairment. Faceplates may be attached to the gantry to accommodate handlebar attachment. The handlebars can be fabricated in different sizes to conform to the dimensions of the gantry.

Accordingly, the invention presents an adjunct for new and existing CT scanners that will greatly enhance the quality and efficiency of the CT process. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
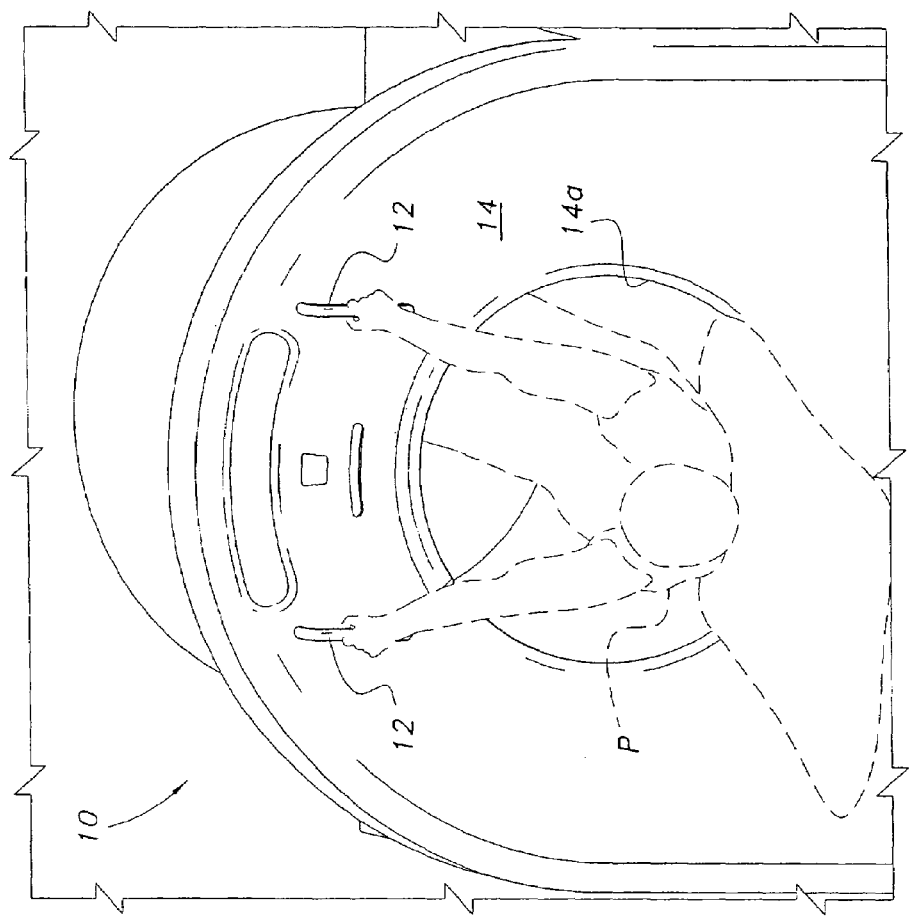
FIG. 1 is an environmental, perspective view of a first embodiment of handlebars for a computed tomography scanner according to the present invention.

Attention is first directed to FIG. 1, wherein a first embodiment of handlebars for a computed tomography (CT) scanner is illustrated. This embodiment includes a pair of handlebars 12 having longitudinal axes vertically-oriented on the front face of gantry 14 of a CT scanner, generally indicated at 10. Each handlebar 12 is a substantially U-shaped bar having opposite ends fastened or fixed to the gantry 14. An opening 14a (conventional) is formed in the gantry to receive a patient P. Handlebars 12 are laterally spaced and positioned above opening 14a. This arrangement allows patient P to grasp handlebars 12 in a manner that will permit the patient to hold his/her arms extended during the CT process. As discussed above, this arm position will enhance the comfort of both impaired and unimpaired patients during the scanning process. The CT scanner and gantry are conventional.

Figure 2:
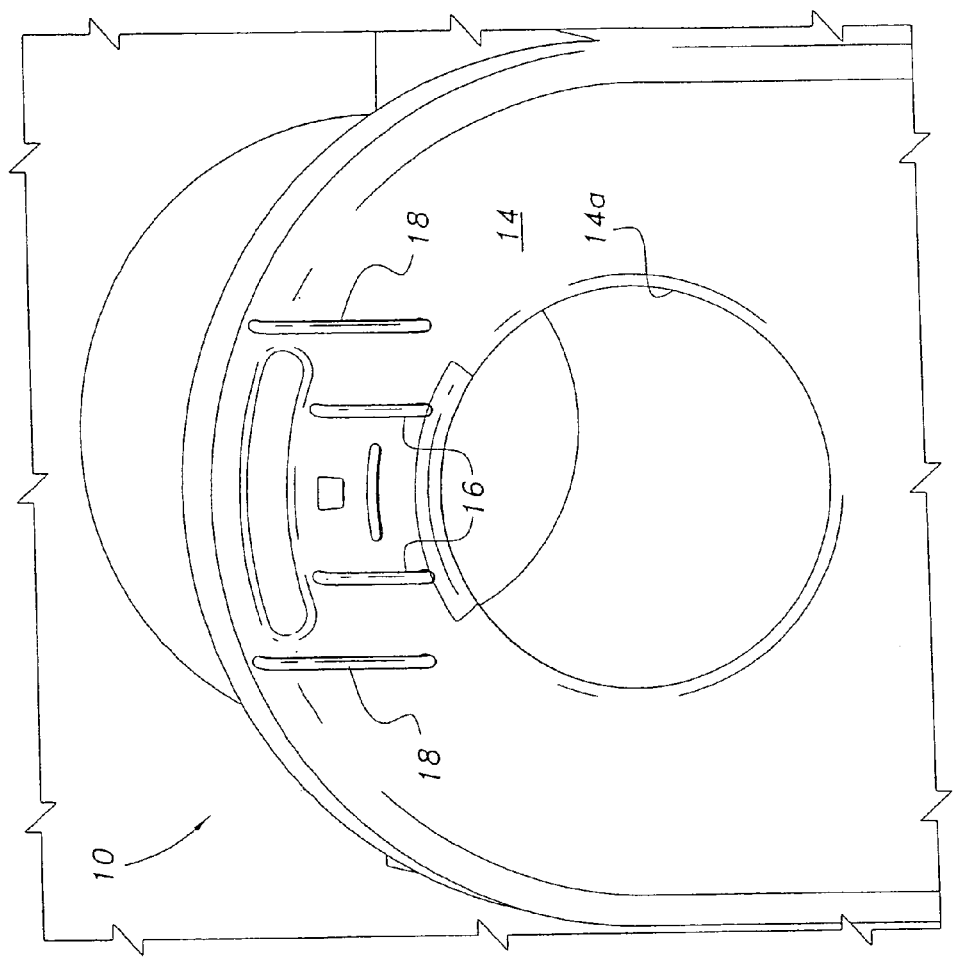
FIG. 2 is a perspective view of a second embodiment of handlebars for a computed tomography scanner according to the present invention.

A second embodiment of the handlebars is shown in FIG. 2. In this embodiment, inner and outer pairs of laterally spaced handlebars 16 and 18 are disposed on the gantry 14. Each pair has its longitudinal axis vertically oriented on the face of gantry 14 of the CT scanner 10. Employing inner and outer handlebars permits accommodating patients having longer or shorter arm lengths. More handle pairs could be employed, if desired.

Figure 3:
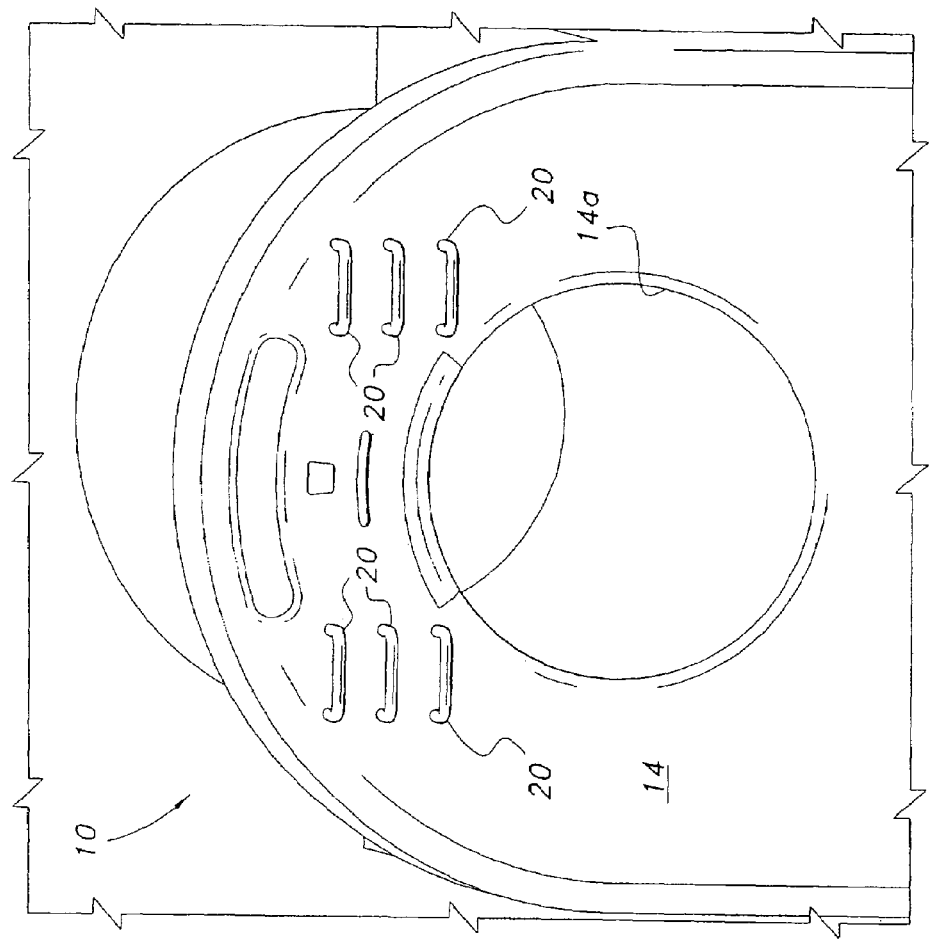
FIG. 3 is a perspective view of a third embodiment of handlebars for a computed tomography scanner according to the present invention.

As best seen in FIG. 3, a third embodiment of the handlebars employs a plurality of handlebars 20 disposed in columns positioned above opening 14a. The longitudinal axis of each handlebar 20 is horizontally oriented on the face of gantry 14. Handlebars 20 are arranged in a ladder-rung fashion. It should be noted that the arrangement is not limited to a three-rung tier.

Figure 4:
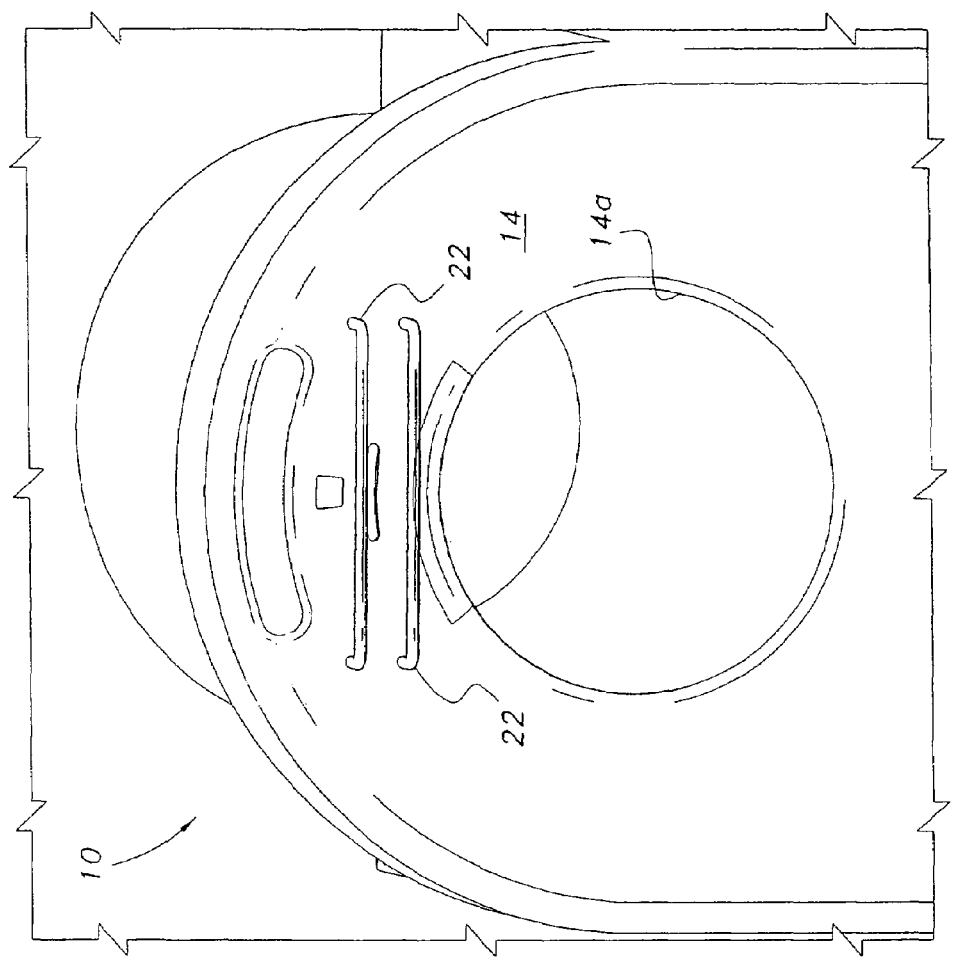
FIG. 4 is a perspective view of a fourth embodiment of handlebars for a computed tomography scanner according to the present invention.

The arrangement of FIG. 4 is similar to that of FIG. 3 in that the longitudinal axes of the handlebars 22 are horizontally oriented on the face of gantry 14 of a CT scanner 10. However handlebars 22 are positioned immediately above opening 14a. As noted above, the arrangement is not limited to any particular number of tiers.

Figure 5:
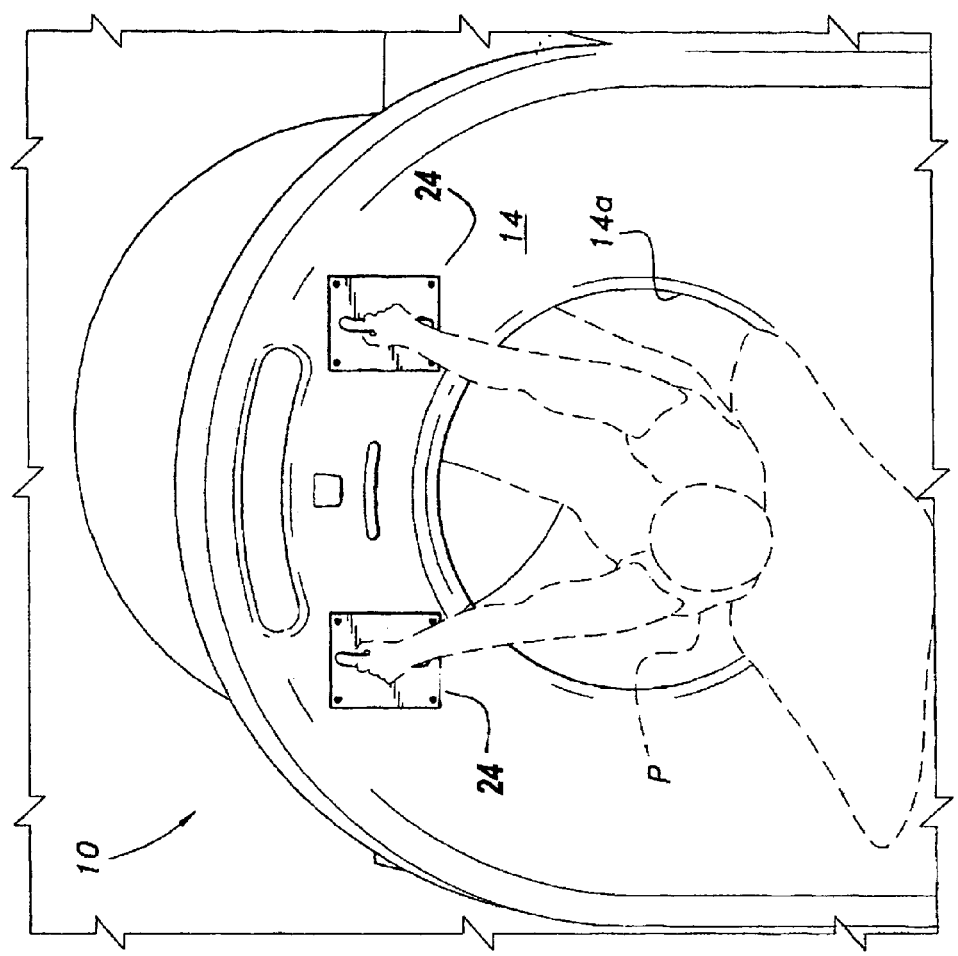
FIG. 5 is a perspective view of a fifth embodiment of handlebars for a computed tomography scanner according to the present invention.

FIG. 5 is illustrative of an embodiment of the handlebars wherein face plates 24 are mounted on the face of gantry 14. Any suitable fasteners (screws, rivets, etc.) may be employed to mount the face plates. The U-shaped handlebars 12 are attached to the face plates. Although the U-shaped bars as illustrated are vertically oriented, it should be recognized that the handle bars could be attached in other positions if desired.

Figure 6:
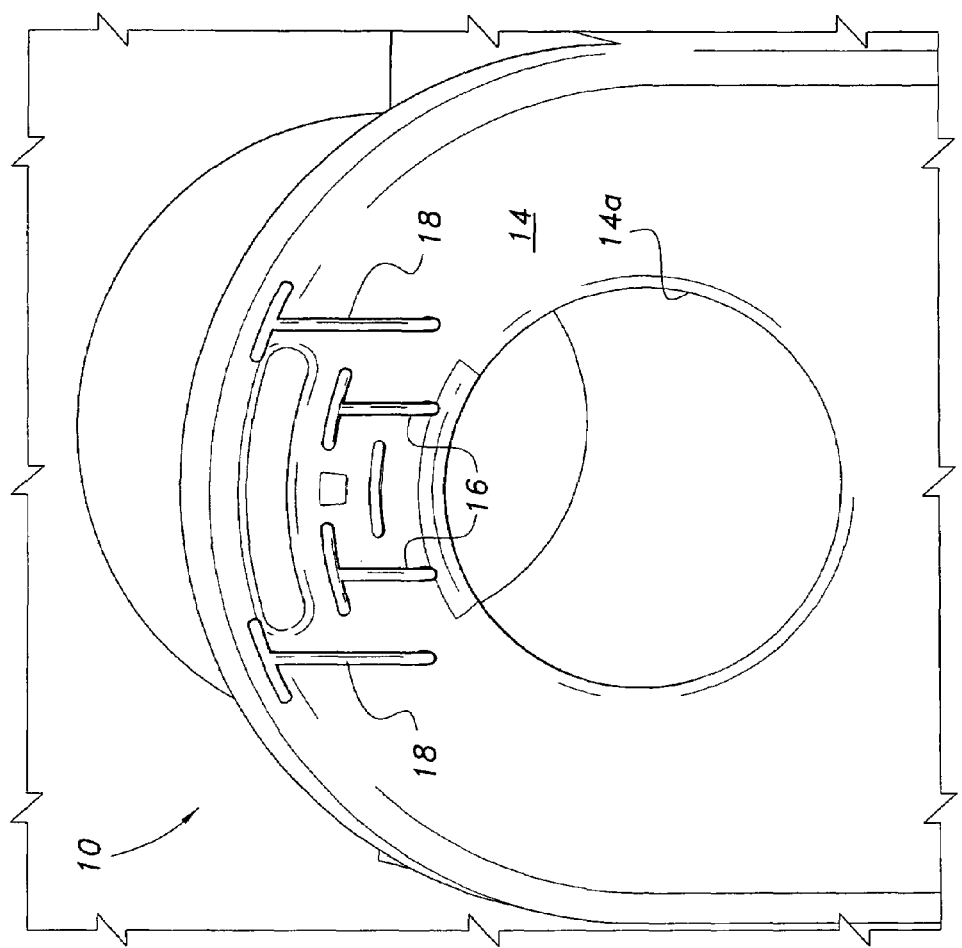
FIG. 6 is a perspective view of a sixth embodiment of handlebars for a computed tomography scanner according to the present invention.

FIG. 6 discloses an embodiment of the handlebars wherein horizontally oriented U-shaped bars are positioned to intersect vertical bars 18, 16 forming a substantial T-shaped configuration. This arrangement allows the patient more latitude when positioning his/her arms during the CT process.

It is to be understood that the present invention is not limited to the embodiments described above, but encompasses any and all embodiments within the scope of the following claims.

We claim:

1. A computed tomography (CT) scanner with handlebars, comprising:
    a CT scanner having a gantry, an entrance to the gantry, and a front face; and
    a plurality of U-shaped bars having opposing ends fastened to the front face of the gantry, the U-shaped bars forming handlebars adapted for gripping by a patient.

2. The computed tomography (CT) scanner with handlebars according to claim 1, wherein said U-shaped bars have longitudinal axes vertically oriented on said front face.

3. The computed tomography (CT) scanner with handlebars according to claim 1, wherein said U-shaped bars have longitudinal axes horizontally oriented on said front face.

4. The computed tomography (CT) scanner with handlebars according to claim 1, wherein said U-shaped bars are attached to face plates, the face plates being fastened to the front face of said gantry.

5. The computed tomography (CT) scanner with handlebars according to claim 1, wherein said U-shaped bars have longitudinal axes horizontally oriented on the front face, said U-shaped bars being positioned immediately above said entrance.

6. The computed tomography (CT) scanner with handlebars according to claim 1, wherein said U-shaped bars have longitudinal axes that are horizontally oriented and including respective vertically oriented bars intersecting each respective U-shaped bar in a substantially T-shaped configuration.

7. The computed tomography (CT) scanner with handlebars according to claim 1, wherein said U-shaped bars are arranged in ladder-rung configurations.

8. A computed tomography (CT) scanner with handlebars, comprising:
    a CT scanner having a gantry, the gantry having an entrance and a front face; and
    a plurality of U-shaped bars having opposing ends fastened to the front face of the gantry, the U-shaped bars being laterally spaced and positioned above the entrance thereby forming handlebars adapted for gripping by a patient.

9. The computed tomography (CT) scanner with handlebars according to claim 8, wherein said U-shaped bars have longitudinal axes vertically oriented on said front face.

10. The computed tomography (CT) scanner with handlebars according to claim 8, wherein said U-shaped bars have longitudinal axes horizontally oriented on said front face.

11. The computed tomography (CT) scanner with handlebars according to claim 8, wherein said U-shaped bars are attached to face plates, the face plates being fastened to the front face of said gantry.

12. The computed tomography (CT) scanner with handlebars according to claim 8, wherein said U-shaped bars have longitudinal axes that are horizontally oriented and including respective vertically oriented bars intersecting each respective U-shaped bar in a substantially T-shaped configuration.

13. The computed tomography (CT) scanner with handlebars according to claim 8, wherein said U-shaped bars are arranged in ladder-rung configurations.

14. Handlebars for a computed tomography (CT) scanner having a gantry and an entrance to the gantry, the handlebars comprising a plurality of bars having opposing ends adapted for fastening to the scanner above the entrance to the gantry of the scanner, the bars forming handlebars adapted for gripping by a patient.

* * * * *